United States Patent [19]

Gonzalez

[11] 4,452,895

[45] Jun. 5, 1984

[54] NON-LACTOSE FERMENTING *PEDIOCOCCUS PENTOSACEUS*

[75] Inventor: Carlos F. Gonzalez, Sarasota, Fla.

[73] Assignee: Microlife Genetics, Sarasota, Fla.

[21] Appl. No.: 359,080

[22] Filed: Mar. 17, 1982

[51] Int. Cl.³ .................. C12N 1/20; C12N 15/00; C12P 7/56; C12R 1/01; C12N 1/100; A23L 1/31

[52] U.S. Cl. ............................ 435/253; 435/172.1; 435/139; 435/822; 435/317; 426/7; 426/55; 426/59

[58] Field of Search ............... 426/7, 55, 59; 435/139, 435/172, 253, 317, 822

[56] References Cited

U.S. PATENT DOCUMENTS 4,238,513 12/1981 Satz .
4,303,679 12/1981 Raccach .

OTHER PUBLICATIONS

Terzaghi, Betty R., Improved Medium for Lactic Streptococci and their Bacteriophages: Applied Microbiol. 29, 807 (1975).
LeBlanc, Donald J., Rapid Screening Procedure for Detection of Plasmids in Streptococci: J. Bacteriol, 140, 1112 (1978).
Bergy's Manual of Determinative Bacteriology, 8th Edition, Buchanan et al., (Ed.), Williams & Wilkins Co., Baltimore, 1974, p. 515.
Anderson et al: J. Bacteriol. 129, 367 (1977).
Efstathiou et al: J. Bacteriol. 130, 257 (1977).

*Primary Examiner*—Thomas G. Wiseman
*Assistant Examiner*—James Martinell
*Attorney, Agent, or Firm*—Ian C. McLeod

[57] ABSTRACT

New strains of non-lactose fermenting *Pediococcus pentosaceus* containing a naturally occurring plasmid are described. The new *Pediococcus pentosaceus* strains have been exposed to a mutagenic agent, preferably 1-methyl-3-nitro-1-nitrosoguanidine, to modify genetic material which controls the fermentation of lactose to lactic acid. The naturally occurring plasmid is between about 30 to 35 megadaltons in molecular weight. Compositions including the new strains of lactose negative *Pediococcus pentosaceus* are useful for food fermentations, particularly meat formulations.

18 Claims, No Drawings

NON-LACTOSE FERMENTING *PEDIOCOCCUS PENTOSACEUS*

BACKGROUND OF THE INVENTION

The present invention relates to new strains of *Pediococcus pentosaceus* useful for fermenting meat. *Pediococcus pentosaceus* strains are no longer able to ferment lactose to produce lactic acid.

PRIOR ART

The present invention relates to an improvement of the invention described in U.S. Pat. No. 4,303,679 to Raccach wherein *Pedicoccus pentosaceus* NRRL-B-11,465 is described for meat fermentations in the presence of a stimulatory metal ion. U.S. Pat. No. 4,238,513 to Satz describes the same strain without the stimulatory metal salts.

As described in U.S. Pat. No. 4,303,679 to Raccach, the stimulatory metal ions, particularly manganese ions, with *Pediococcus pentosaceus* NRRL-B-11,465 provide significant advantage in commercial meat fermentations. The fermentations are rapid at low temperatures which is an economic and processing advantage. One problem which has been encountered is that when there are significant amounts of lactose in the meat formulations, because of added fillers or bulking agents, the pH of the fermented meat drops to too low a level (i.e. below pH 4.6) and the fermented meat tastes sour. This is particularly a problem with hams and sausages.

OBJECTS

It is therefore an object of the present invention to provide new strains of *Pediococcus pentosaceus* which do not have the ability to ferment lactose. It further is an object of the present invention to provide bacterial compositions including the new strains, which are stable upon storage so as to maintain a good capability for producing lactic acid and which will not revert to having the ability to ferment lactose as a function of time as a result of storage. It is further an object of the present invention to provide a method for producing the new strains using a mutagenic agent. These and other objects will become increasingly apparent from the following description.

GENERAL DESCRIPTION

The present invention relates to a new storage stable strain of *Pediococcus pentosaceus* adapted for food fermentations and containing a naturally occurring plasmid and which is unable to ferment lactose to lactic acid as a result of modification of generic material controlling lactose fermentation in a known strain of *Pediococcus pentosaceus*. The invention further relates to an improvement in the method for preparation of a fermented food by providing a culture in the food and then fermenting which comprises: providing in the food a strain of a *Pediococcus pentosaceus* containing a naturally occurring plasmid and which is unable to ferment lactose to lactic acid as a result of modification of genetic material controlling lactose fermentation in a known strain of *Pediococcus pentosaceus*. The single naturally occurring plasmid in the known *Pediococcus pentosaceus* measures between about 30 to 35 megadaltons in molecular weight. The preferred new non-lactose fermenting strain is *Pediococcus pentosaceus* NRRL-B-15008. The new strains can be characterized as pla+ (plasmid positive) and lac− (lactose negative).

The invention also relates to a method of modifying genetic material controlling lactose utilization in a known strain of *Pediococcus pentosaceus* having the ability to ferment lactose to lactic acid and containing a naturally occurring plasmid which comprises contacting viable known strain cells of *Pediococcus pentosaceus* with a sub-lethal concentration of a mutagenic agent. The pla+, lac− *Pediococcus pentosaceus* strains produced are adapted for the food fermentations.

To prepare the new strains, a pla+, suc+, lac+ *Pediococcus pentasaceus* was used. The naturally occurring species has at least one commercially useful natural strain which is pla+, suc+, lac+ *Pediococcus pentosaceus* NRRL-B-11,465. The strain is particularly useful at low temperatures. The pla+, suc+, lac+ *Pediococcus pentosaceus* was treated with a mutagenic agent at a sub-lethal concentration so that it was not killed and various new pla+, suc+, lac− *Pediococcus pentosaceus* strains were produced. Suitable mutagenic agents are for instance 1-methyl-3-nitro-1-nitrosoguanidine at sub-lethal concentrations in a liquid medium.

A plasmid profile was determined by lysis and agarose gel electrophoresis on the parent strain and the new strains as described in LeBlanc et al, *J. of Bacteriology* Vol 140, No. 3, pages 1112 to 1115 (1979). It was found that the single natural plasmid remained after exposure to the mutagenic agent. The plasmid was about 33 megadaltons in molecular weight based upon comparisons with known size standards in parallel electrophoresis patterns.

The resulting pla+, suc+, lac− *Pediococcus pentosaceus* were concentrated to at least about $1 \times 10^8$ cells per ml. Manganese ions were added and the concentrate was used to produce pepperoni containing lactose as described in Raccach U.S. Pat. No. 4,303,679. Preferably the new pla+, suc+, lac− strains were used in substantially pure form but can be mixed with other food fermenting bacteria as is known in the prior art. It was found that such strains were somewhat slower that pla+, suc+, lac+ *Pediococcus pentosaceus* NRRL-B-11,465; however, they were still commercially useful as can be seen from the Example.

Various culture preservation agents can be used as is known in the prior art. Glycerol is preferred for frozen concentrates as a freezing stabilizing agent. Lyophilized bacterial concentrates can also be used.

SPECIFIC DESCRIPTION

The following example shows the steps in the isolation of pla+, suc+, lac− *Pediococcus pentosaceus* NRRL-B-15008 from pla+, suc+, lac+ *Pediococcus pentosaceus* NRRL-B-11465.

EXAMPLE 1

(a) Grow the *Pediococcus pentosaceus* NRRL-B-11,465 overnight in M17 broth containing glucose but not sodium glycerophosphate as described by Terzaghi et al in Applied Microbiology Vol. 29, No. 6 p. 807 (June 1976) until attain O.D. 0.8 (at 600 nm.);

(b) Inoculate *Pediococcus pentosaceus* NRRL-B-11,465 into tubes of citrate buffer (0.5 M, pH 5.4) containing increasing concentrations of 1-methyl-3-nitro-1-nitrosoguanidine. Incubate at 35° C. for various time intervals and determine viable cell count. Incubation at 35° C. for 40 minutes in presence of 1200 μg of 1-methyl-3-nitro-1-nitrosoguanidine resulted in a reduction of *Pediococcus pentosaceus* viable cell count from $10^7$ c.f.u. per ml to $10^2$ c.f.u. per ml.

(c) A Basal Sugar Medium (BSM) was used for plating of surviving *Pediococcus pentosaceus* to determine lactose fermentation. Fermentation of carbohydrates added to the medium is shown by color change of a purple color to yellow as a result of the lowered pH. The pH change occurs at pH 5.2. BSM is:

| | | |
|---|---|---|
| Tryptone | 20 | grams |
| Yeast Extract | 5 | grams |
| Gelatin | 2.5 | grams |
| Sodium Acetate | 1.5 | grams |
| Agar | 15 | grams |
| 0.4% Bromocresol purple | (BCP) | |
| Water | 1000 | ml |

After heat treatment of 15 minutes at 121° C., a filter-sterilized (0.22μ filter) solution of concentrated carbohydrate (20% w/v) was aseptically added to give a final concentration of 0.5% (w/v) carbohydrate in the BSM medium. The medium was aseptically poured into Petri dishes and allowed to solidify at room temperature. Supplemental carbohydrates added to Medium (BSM) for determining sugar fermentation characteristics were:
BSM+lactose=BL
BSM+sucrose=BS (d) The surviving *Pediococcus pentosaceus* cells were plated on BL agar to detect lac⁻ strains which do not produce lactic acid from lactose.

(e) The BL agar plates were incubated 48 hours at 32° C. and lac⁻ strains were picked and streaked on APT agar (Difco$_{t.m.}$ Cat. No. 0654) to obtain purified, single colony isolates; and (f) These colonies were inoculated into BL broth and BSM (no added carbohydrate) broth, and were incubated 15 days at 32° C.

(g) *Pediococcus pentosaceus* NRRL-B-15008 was selected for further testing from BL broth culture which showed no acid formation after 15 days at 32° C.

Using the LeBlanc et al procedure, an agarose gel electrophoresis pattern was performed on *Pediococcus pentosaceus* NRRL-B-15008 in comparison to *Pediococcus pentosaceus* NRRL-B-11465. The results showed that *Pediococcus pentosaceus* NRRL-B-11465 and *Pediococcus pentosaceus* NRRL-B-15008 contained comparable plasmid profiles.

The carbohydrate fermentation pattern of pla⁺, suc⁺, lac⁻ *Pediococcus pentosaceus* NRRL-B-15008 is shown in Table I by comparison to the parent strain NRRL-B-11465 as described in U.S. Pat. No. 4,303,679 to Raccach.

The carbohydrate fermentation patterns indicate that the ability to utilize lactose was the main difference of NRRL-B-15008 in comparison to NRRL-B-11465.

TABLE I

| | REACTION | | (BBL MINITEK ® SYSTEM) | |
|---|---|---|---|---|
| SUBSTRATE | POSITIVE | NEGATIVE | NRRL-B-11465 | NRRL-B-15008 |
| Adonitol | yel to yellow orange | Red orange | − | − |
| Arabinose | yel to yellow orange | Red orange | + | + |
| Cellobiose | yel to yellow orange | Red orange | + | + |
| Dextrose | yel to yellow orange | Red orange | + | + |
| Dulcitol | yel to yellow orange | Red orange | − | − |
| Galactose | yel to yellow orange | Red orange | + | + |
| Glycerol | yel to yellow orange | Red orange | ∓ | ∓ |
| Inositol | yel to yellow orange | Red orange | − | − |
| Lactose | yel to yellow orange | Red orange | + | − |
| Maltose | yel to yellow orange | Red orange | + | + |
| Mannitol | yel to yellow orange | Red orange | − | − |
| Mannose | yel to yellow orange | Red orange | + | + |
| Melibiose | yel to yellow orange | Red orange | + | + |
| Nitrate reductase | dark rust-red | Yellow, white or pink | − | − |
| ONPG | light yellow | White | − | − |
| Raffinose | yel to yellow orange | Red orange | + | + |
| Rhamnose | yel to yellow orange | Red orange | ± | ± |
| Salicin | yel to yellow orange | Red orange | ± | ± |
| Sorbitol | yel to yellow orange | Red orange | − | − |
| Sucrose | yel to yellow orange | Red orange | + | + |
| Trehalose | yel to yellow orange | Red orange | + | + |
| Xylose | yel to yellow orange | Red orange | − | − |
| Starch | yel to yellow orange | Red orange | + | + |
| Esculin | brown | Off white | + | + |
| Lysine | yellow | | + | + |
| Arginine | yellow | | + | + |

Bacterial Concentrates

Bacterial concentrates of NRRL-B-11465 and NRRL-B-15008 were prepared as described in U.S. Pat. No. 4,303,679 to Raccach. The cells were grown in the following medium:

| | | |
|---|---|---|
| Yeast extract | 210 | grams |
| Dextrose | 500 | grams |
| Corn Steep | 500 | grams |
| Magnesium sulfate | 0.264 | grams |
| Manganese sulfate | 0.264 | grams |
| Ferric sulfate | 0.264 | grams |
| Water to 10 liters. | | |

The pH was adjusted to 6.8 with ammonia. The pH was maintained at about 6.0 with continuous pH adjustment during growth by adding ammonia. The cells were grown to about $1 \times 10^{10}$ cells per ml. The cells were concentrated by centrifugation and the pellet was resuspended with supernatant medium to 1/10 of the original volume and glycerin was added to a final concentration of 10% (W/W). Manganese sulfate (18.4 g of 36.96% (W/W) solution to 100 grams of concentrate) was added to the concentrate. The concentrate was frozen for storage pair to use and was found to be storage stable. The concentrate contained about $2 \times 10^{11}$ cells per ml.

Sausage Preparation

Pepperoni sausage was made using pla+, suc+, lac− *Pediococcus pentosaceus* NRRL-B-15008 and pla+, suc+, lac+ *Pediococcus pentosaceus* NRRL-B-11465. The meat formulation was 2542 grams of pork plus 1090 grams of beef coarsely chopped to which was added:

| Salt 119.85 grams total (3.3%) by weight including: | |
| --- | --- |
| BHA | 1.1 ml (0.003% soln 10% w/v) |
| BHT | 1.1 ml (0.003% soln 10% w/v) |
| Sodium citrate | 1.1 ml (0.003% soln 10% w/v) |
| Dextrose | 21.8 (0.6% by weight based on meat) |
| Lactose | 108.9 g (3.0% by weight based on meat) |
| Pepperoni spice mix | 20.0 g |
| Sodium nitrite | 2.8 ml (200 mg/ml water solution) |

The culture concentrate was added at about $4 \times 10^7$ cells per gram of the meat formulation. The manganese ion was present in the amount of about 4 ppm in the meat formulation. The inoculated meat mixture was stuffed into fibrous pepperoni casing and incubated at 32° C. internal temperature at 80% relative humidity. The results are shown in Table II.

TABLE II

| | pH | |
| --- | --- | --- |
| Time Hours | pla+, suc+, lac+ Control-NRRL-B-11465 + Mn | pla+, suc+, lac− NRRL-B-15008 + Mn |
| 0.0 | 6.01 | 6.01 |
| 11.0* | 5.41 | 5.95 |
| 13.0 | 4.97 | 5.73 |
| 16.0 | 4.90 | — |
| 16.5 | — | 5.21 |

*After 11 hours incubation the internal meat temperature was 32° C. (90° F.).

The result, as can be seen from Table II, is that the pla+, suc+, lac− NRRL-B-15008 performed well but somewhat more slowly than pla+, suc+, lac+ NRRL-B-11465. Organoleptically the NRRL-B-15008 pepperoni sausage was indistinguishable from that made with NRRL-B-11465, providing the pH was about 5.2–5.3. The pH of 4.9 in Table II for NRRL-B-11465 is too low and is not acceptable. The reason the pH for NRRL-B-15008 did not drop to an unacceptable level is because lactose is not fermented.

I claim:

1. A storage stable biologically pure culture of *Pediococcus pentosaceus* adapted for food fermentations and containing a naturally occurring plasmid and which strain is unable to ferment lactose to lactic acid as a result of mutagenic modification of genetic material controlling lactose fermentation in a known strain of *Pediococcus pentosaceus* also containing the plasmid and which strain is able to ferment dextrose to lactic acid in a food.

2. The modified culture of claim 1 containing at least about $10^6$ cells per ml.

3. The modified culture of claim 1 wherein the known strain which has been subjected to mutagenic modification is *Pediococcus pentosaceus* NRRL-B-11,465.

4. A composition which comprises a storage stable biologically pure culture of a *Pediococcus pentosaceus* containing a naturally occurring plasmid measuring between about 30 to 35 megadaltons which composition is unable to ferment lactose to lactic acid as a result of mutagenic modification of genetic material controlling lactose fermentation in a known strain of *Pediococcus pentosaceus* also containing the plasmid and a preservation agent for the culture and the composition is able to ferment dextrose to lactic acid in a food.

5. The composition of claim 4 wherein the preservation agent is a freezing stabilizing agent which maintains viable cells and wherein the composition is frozen.

6. The modified culture of claim 1 which is the strain *Pediococcus pentosaceus* NRRL-B-15008.

7. In the method for preparation of a fermented food by providing a culture in the food and then fermenting the food the improvement which comprises: providing in the food a strain of *Pediococcus pentosaceus* containing a naturally occurring plasmid and which strain is unable to ferment lactose to lactic acid as a result of the mutagenic modification of genetic material controlling lactose fermentation in a known strain of *Pediococcus pentosaceus* also containing the plasmid, wherein the fermentation is conducted in the food in the presence of lactose which is not fermented to lactic acid and dextrose which is fermented to produce lactic acid which lowers pH of the food.

8. The method of claim 7 wherein the modified strain of *Pediococcus pentosaceus* provided in the food is *Pediococcus pentosaceus* NRRL-B-15008 and wherein the food is a fermented meat.

9. The method of claim 7 wherein the modified strain provided in the food is a biologically pure strain of *Pediococcus pentosaceus* which does not ferment lactose to produce lactic acid.

10. The method of claim 7 wherein the naturally occurring plasmid is about 30 to 35 megadaltons in molecular weight.

11. The method of claim 7 wherein the *Pediococcus pentosaceus* which is unable to ferment lactose to lactic acid has been exposed to a sub-lethal amount of a mutagenic agent.

12. The method of claim 11 wherein the mutagenic agent is 1-methyl-3-nitro-1-nitrosoguanidine.

13. The method of claim 7 wherein the known strain which has been subjected to mutagenic modification is *Pediococcus pentosaceus* NRRL-B-11465.

14. The method of claim 13 wherein the mutagenic modification produces a strain having the fermentation characteristics of *Pediococcus pentosaceus* NRRL-B-15008.

15. The composition of claim 4 in admixture with a metal ion which stimulates growth of the modified strain.

16. The modified strain of claim 15 wherein the metal ion is manganese ion.

17. The method of claim 7 wherein the modified strain is in admixture with a metal ion which stimulates the growth of the modified strain.

18. The method of claim 17 wherein the metal ion is a manganese ion.

* * * * *